US012303210B2

(12) United States Patent
Collet et al.

(10) Patent No.: US 12,303,210 B2
(45) Date of Patent: May 20, 2025

(54) SURGICAL IMPACTOR ARRAYS

(71) Applicant: DePuy Synthes Products, Inc., Raynham, MA (US)

(72) Inventors: Hervé Collet, Chatenay (FR); Nicolas Demanget, Saint-Egréve (FR); Grégory Dez, Grenoble (FR); Anthony Leandri, Isére (FR); Arnaud Robert, Isére (FR)

(73) Assignee: DePuy Synthes Products, Inc., Raynham, MA (US)

( * ) Notice: Subject to any disclaimer, the term of this patent is extended or adjusted under 35 U.S.C. 154(b) by 622 days.

(21) Appl. No.: 17/542,194

(22) Filed: Dec. 3, 2021

(65) Prior Publication Data

US 2023/0172668 A1 Jun. 8, 2023

(51) Int. Cl.
*A61B 34/20* (2016.01)
*A61B 17/00* (2006.01)
*A61B 17/92* (2006.01)
*A61B 34/30* (2016.01)

(52) U.S. Cl.
CPC .............. *A61B 34/20* (2016.02); *A61B 17/92* (2013.01); *A61B 34/30* (2016.02); *A61B 2017/00367* (2013.01); *A61B 2017/00477* (2013.01); *A61B 2017/924* (2013.01); *A61B 2034/2055* (2016.02)

(58) Field of Classification Search
CPC . A61B 34/20; A61B 34/30; A61B 2034/2055; A61B 17/92; A61B 2017/00367; A61B 2017/00477; A61B 2017/924
See application file for complete search history.

(56) References Cited

U.S. PATENT DOCUMENTS

| 8,961,500 | B2 | 2/2015 | DiCorleto et al. |
| 9,451,999 | B2 | 9/2016 | Simpson et al. |
| 10,743,950 | B2 | 8/2020 | Constantinos et al. |

(Continued)

FOREIGN PATENT DOCUMENTS

| DE | 10146042 A1 | 5/2003 |
| DE | 10-2007-014-737 A1 | 9/2008 |

(Continued)

*Primary Examiner* — Chao Sheng
(74) *Attorney, Agent, or Firm* — Condo Roccia Koptiw LLP

(57) ABSTRACT

Systems, methods, and devices are disclosed for navigational arrays for attaching to surgical tools, the arrays comprising a frame comprising fiducials for detection by an optical navigation system, and a body having a first end for supporting the frame and a second end defining an opening, wherein the opening is aligned with a first axis of the surgical tool, wherein the opening engages a stationary surface adjacent to the surgical tool, and wherein the opening engages features disposed at predetermined even intervals on the stationary surface adapted to allow repositioning of the array from a first position to a second position, wherein the second position is at least one of a rotational offset or an axial offset from the first position. The stationary surface may be a step disposed on an adapter inserted into the surgical tool. The stationary surface may be a sheath covering a rotatable shaft inserted into the surgical tool. The stationary surface may be a sleeve disposed on the surgical tool. The arrays may be part of a computer-assisted surgical system.

20 Claims, 7 Drawing Sheets

(56) References Cited

U.S. PATENT DOCUMENTS

| | | | |
|---|---|---|---|
| 10,912,655 B2 | 2/2021 | Kambiz et al. | |
| 10,932,840 B2 | 3/2021 | DiCorleto et al. | |
| 11,331,126 B2 | 5/2022 | Cha | |
| 2017/0196707 A1 | 7/2017 | Kambiz et al. | |
| 2018/0344301 A1* | 12/2018 | Wehrli | A61B 34/20 |
| 2021/0007811 A1* | 1/2021 | Troxell | A61B 34/10 |
| 2021/0322081 A1 | 10/2021 | Sweitzer et al. | |

FOREIGN PATENT DOCUMENTS

| | | |
|---|---|---|
| EP | 3763315 A1 | 1/2021 |
| WO | 2020/185032 A2 | 9/2020 |

\* cited by examiner

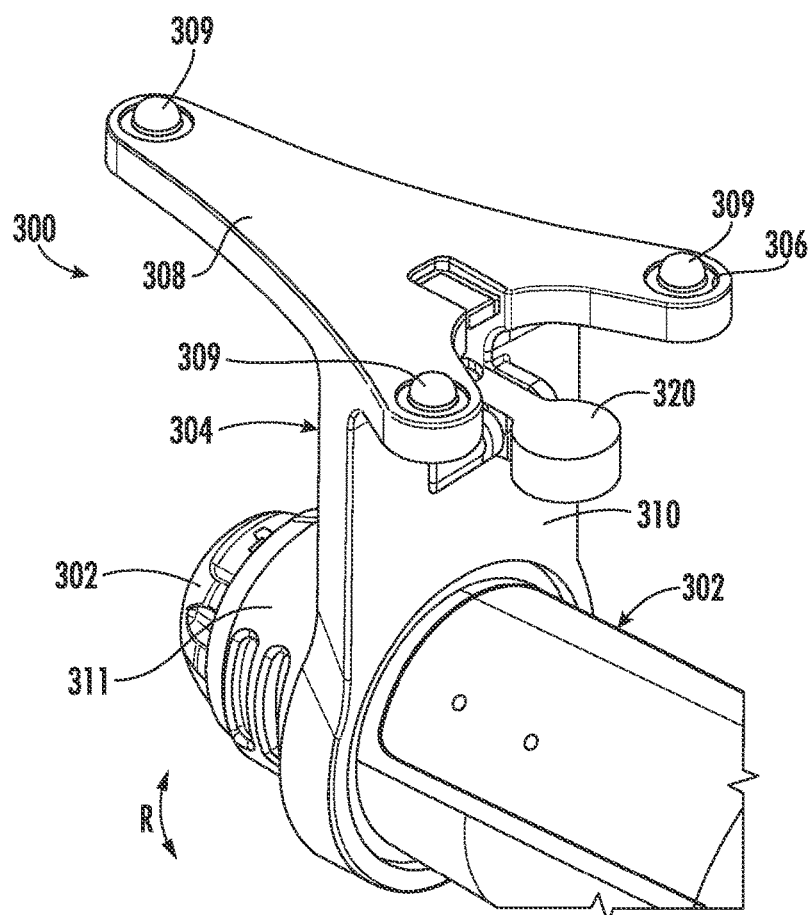
FIG. 3A
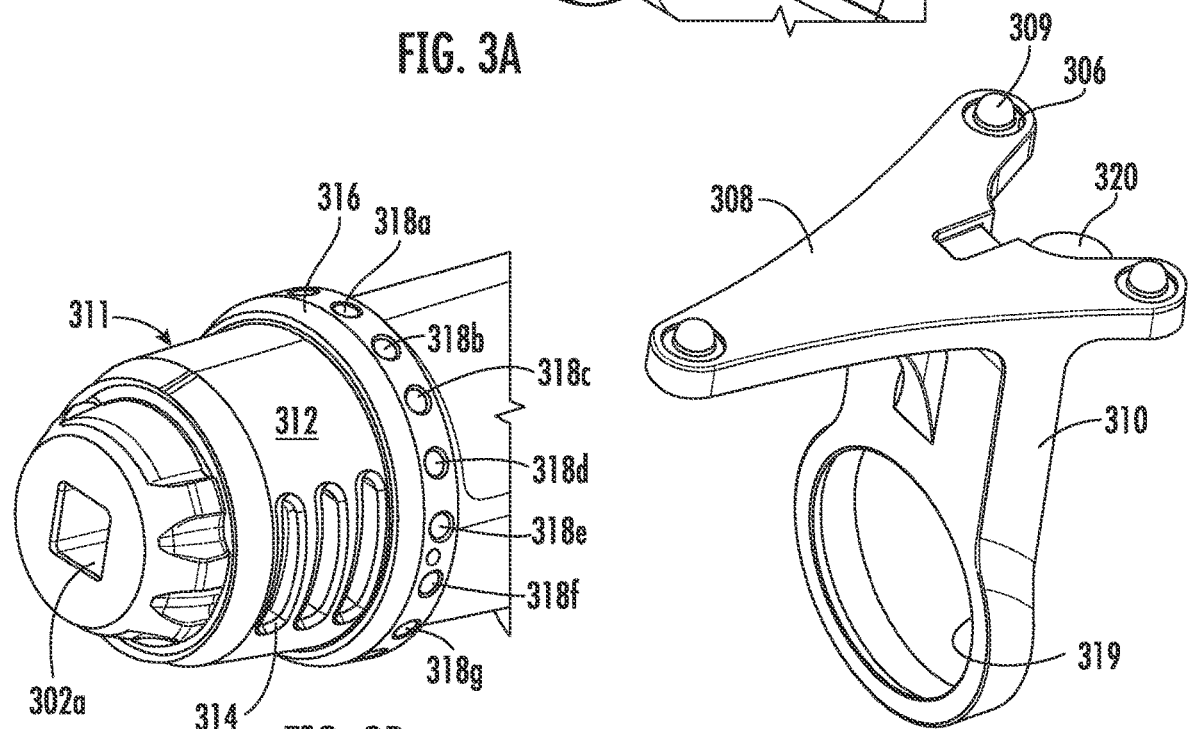
FIG. 3B
FIG. 3C

SURGICAL IMPACTOR ARRAYS

BACKGROUND

Robotic or robot-assisted surgeries have many associated advantages, particularly in terms of placement precision of surgical tools and implants. Possibly one of the most important aspects of a robotic surgical system is its ability to track a position and/or orientation of a tool. Briefly, an array can be coupled to the tool, and fiducials of the array are used to indicate the position and/or orientation of the tool. This is important with computer-assisted navigation, augmented reality, and the like. Since many fiducials are adapted for use with an optical navigation system, line of sight between the array and the navigation system is an important consideration.

However, of primary importance, at least for tools that require manual activation, is the ability of a user (e.g., a surgeon) to set the tool up in a position which she finds comfortable, for example, without having to factor in a position of the array. Alternatively, the tool can be automated, as part of a computer-assisted surgical system comprising a robot, and in such cases, optical interference from peripherals of the system may require adjustment of the array.

Accordingly, there is a need for systems, devices, and methods for arrays that can be re-positioned with respect to at least one axis of the tool.

SUMMARY

Systems, methods, and devices are disclosed for navigational arrays for attaching to surgical tools, the arrays comprising a frame comprising fiducials for detection by an optical navigation system, and a body having a first end for supporting the frame and a second end defining an opening, wherein the opening is aligned with a first axis of the surgical tool, wherein the opening engages a stationary surface adjacent to the surgical tool, and wherein the opening engages features disposed at predetermined even intervals on the stationary surface adapted to allow repositioning of the array from a first position to a second position, wherein the second position is at least one of a rotational offset or an axial offset from the first position. The stationary surface may be a step disposed on an adapter inserted into the surgical tool. The stationary surface may be a sheath covering a rotatable shaft inserted into the surgical tool. The stationary surface may be a sleeve disposed on the surgical tool. The arrays may be part of a computer-assisted surgical system.

BRIEF DESCRIPTION OF THE DRAWINGS

FIG. 3A shows a surgical impactor with another embodiment of an associated array that is configured to be deployed in a plurality of positions;

FIG. 3B shows the surgical impactor of FIG. 3A with the array removed;

FIG. 3C shows the array of FIG. 3A removed from the surgical impactor;

DETAILED DESCRIPTION

Figure 1A:
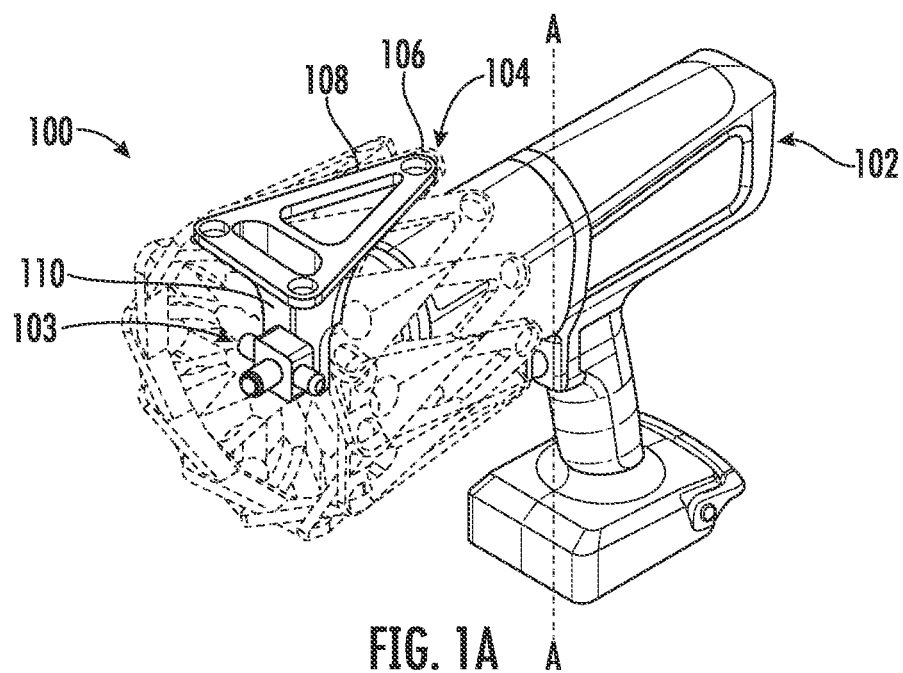
FIG. 1A shows a surgical impactor with an associated array that is configured to be deployed in a plurality of positions.

FIG. 1A illustrates a system 100 including a surgical impactor 102. Surgical impactors, such as the surgical impactor 102, are useful in clinical settings to replace manual impactions (e.g., such as with mallets). Use of the surgical impactor 102 may be beneficial to the user (e.g., a surgeon) in terms of precision and avoiding fatigue, or even avoiding repetitive motion injury. In this embodiment, the surgical impactor 102 may be a conventional surgical impactor, such as a KINCISE™ surgical impactor available from DePuy Synthes, Raynham, MA.

An adaptor 103 is retained in the surgical impactor 102 to engage the patient (not depicted) in a surgical procedure, such as, for example, a hip or knee arthroplasty. For simplicity of explanation, the surgical impactor 102 is depicted as having an axis A, and the adaptor 103 extends perpendicular to the axis A. It should be understood that the surgical impactor 102 does not produce any rotational force on the adaptor 103, but does produce rapid impaction forces along an axis defined by the adaptor (e.g., perpendicular to the axis A). A distal end of the adaptor 103 is not depicted, but it is understood that different adapters have various distal ends, each having a specific shape adapted to a surgical task according to the surgical procedure (e.g., pursuant to a treatment plan). For example, as will be described with respect to FIGS. 2A-2C, there are different distal-ended adapters (e.g., for broaching, etc.). A proximal end of the adaptor 103 is not visible in FIG. 1A, as it is retained within a port (also not visible) of the surgical impactor 102.

An array 104 is associated with the surgical impactor 102 and/or the adaptor 103, and as illustrated in FIG. 1A, the array is disposed between the surgical impactor and the adaptor. For example, a portion of the proximal end of the adaptor 103 may be retained within the port of the surgical impactor 102 in a conventional manner, and the array 104 trapped between the surgical impactor and the adaptor. However, as will be seen with respect to FIGS. 1B and 2A-2C, according to the present disclosure, the adaptor 103 features a component (e.g., a non-continuous shaped step) to engage the array 104 and securely retain it in position.

The array 104 comprises a plurality of sockets 106 defined in a frame 108. The sockets 106 are adapted to receive fiducials (not depicted), for example, the sockets may each receive a single-use reflective navigation marker.

Figure 7:
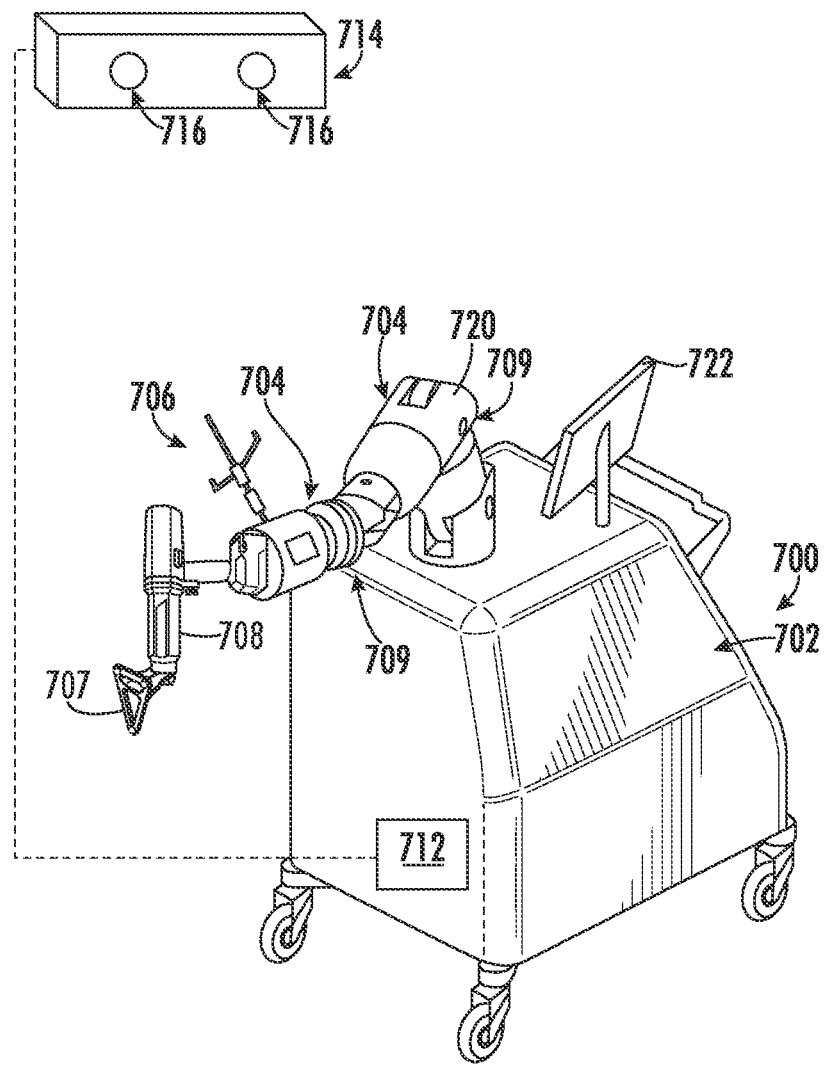
FIG. 7 is a schematic of a computer-assisted surgical system including a surgical robot and an end effector comprising the surgical tool and associated array of FIG. 1A.

The fiducials (e.g., once retained in the sockets 106) may be used as part of a navigation system, as will be described with respect to FIG. 7, however, in summary, the fiducials of the array 104 enable a position and/or orientation of the array to be determined, which can be extrapolated (e.g., such as by a control unit or other logic) to determine a position and/or orientation of the adapter 103 (e.g., with reference to a patient).

As navigation systems typically operate as optical-based systems (e.g., the fiducials disposed in the sockets 106 are adapted for use with an optical navigation system), maintenance of line of sight between the array 104 and the navigation system is important. For example, during use, the surgical impactor 102 should not be interposed between the array 104 and the navigation system (e.g., to prevent interference with line of sight).

Accordingly, the array 104 is configured to be deployed in a plurality of positions with respect to the surgical impactor 102. For example, considering the axis A of the surgical impactor 102, the array 104 is capable of being deployed aligned with A (as depicted in solid lines) or offset by intervals, such as shown in the phantom lines. By way of a non-limiting example, the array 104 may be offset with respect to the axis A of the surgical impactor 102 by intervals of 22.5 degrees, 30 degrees, 45 degrees, etc., as will be explained.

The array 104 also comprises a body 110 which supports the frame 108 and connects the array to the adaptor 103. The body includes a frame support region 116.

Figure 1B:
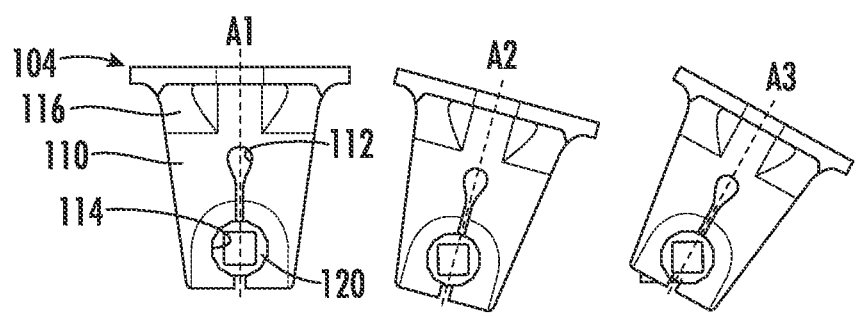
FIG. 1B shows an elevational view of the array of FIG. 1A.

Turning to FIG. 1B, the body 110 of the array 104 has a channel 112 that extends partly along a longitudinal axis A1 of the body. An opening 114 is formed in the channel 112. Preferably, the opening 114 is not a continuous shape. For clarity, examples of continuous shapes would be circles, ovals, and other shapes with no edges. Preferably, the opening 114 has a plurality of features (e.g., edges, protrusions, etc.) for engaging a non continuous shape, such as a regular polygon with a plurality of facets.

A step 120 of the adapter 103 is disposed in the opening 114. The step 120 may tightly fit within the opening 114, for example, a geometry of the channel 112 may cause the body 110 to flex inwards toward the step. The step 120 may feature a plurality of facets, for example to prevent the array 104 from rotating out of position during vibration from use of the surgical impactor 102. As can be appreciated, a number of facets in the plurality of facets of the step 120 corresponds to a number of offset intervals for the array.

For example, the array 104 may be oriented in a first position corresponding to a first axis A1 when the opening 114 of the array is placed over the step 120 of the adapter 103. Due to the geometry of the step 120 (e.g., faceted geometry), the array 104 will be unable to rotate to a new axis while the adaptor 103 is retained in the surgical impactor 102. If a second axis A2 is desired, the opening 114 of the array 104 must be disengaged from the step 120, the array rotated to axis A2, and the opening of the array placed over the step to achieve the axis A2. The axis A1 is offset from the axis A2 by a number of degrees corresponding to the number of facets of the step 120 moved, as depicted, by 30 degrees (e.g., one facet clockwise out of twelve facets). If a third axis A3 is desired, the opening 114 of the array 104 must be disengaged from the step 120, the array rotated to axis A3, and the opening of the array placed over the step to achieve the axis A3. The axis A3 is offset 30 degrees clockwise from the axis A2, and 60 degrees clockwise from the axis A1 (e.g., because there are twelve facets). While the step 120 and opening 114 are depicted in FIG. 1B as a convex polygon, it is understood that other evenly spaced, noncontiguous, shapes are contemplated (e.g., star-shaped, etc.).

Figure 2A:
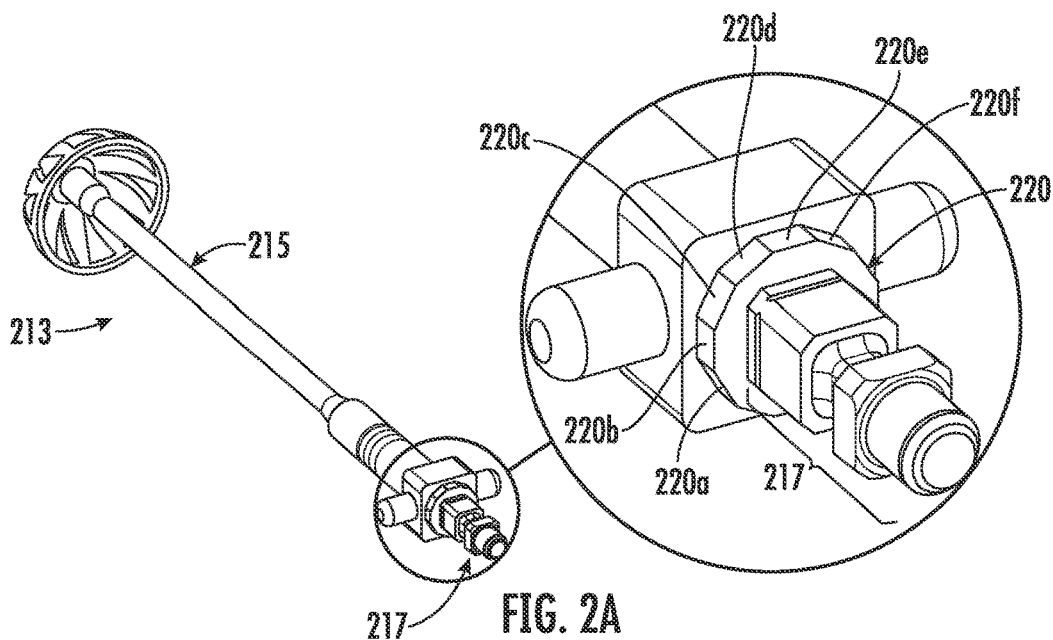
FIG. 2A shows a first adapter for use with the impactor and array of FIG. 1A, including a detail view.

FIG. 2A shows a first adapter 213 for use with the surgical impactor 102 and the array 104 of FIG. 1A. The adapter 213 has a cup-shaped distal portion 215. The adaptor 213 has a proximal portion 217, which may be retained within a port of the surgical impactor 102 of FIG. 1A in a conventional manner. With reference to the detail view, between the distal portion 215 and the proximal portion 217, a step 220 is provided on the adapter 213. The step 220 may have a non continuous shape, such as a regular polygon with a plurality of facets 220a-f. As can be appreciated, a number of facets in the plurality of facets 220a-f of the step 220 corresponds to a number of offset intervals for the array 104 (e.g., offset relative to a given axis A of the surgical impactor 102). Although not visible, other facets are provided on the step 220 so that the facets are disposed at even intervals around the entire circumference of the step.

Figure 2B:
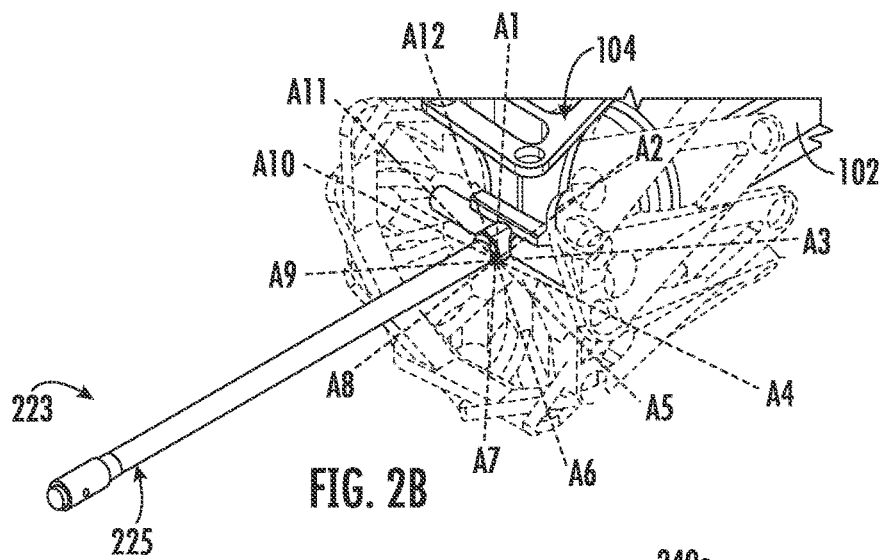
FIG. 2B shows a second adapter for use with the impactor and array of FIG. 1A.

Turning now to FIG. 2B, a second adapter 223 for use with a surgical impactor and an array (such as the surgical impactor 102 and the array 104 of FIG. 1A) has a blunt distal portion 225. The adaptor 223 has a proximal portion retained within a port of a surgical impactor (e.g., such as the surgical impactor 102 of FIG. 1A) in a conventional manner. Between the distal portion 225 and the proximal portion, a step (not visible) is provided on the adapter 223. The step may have a non continuous shape, such as a regular polygon with a plurality of facets. As can be appreciated, when an array (such as the array 104 of FIG. 1A) is mounted on the step, a number of facets in the plurality of facets of the step corresponds to a number of offset intervals (e.g., potential axes A1-A12 in FIG. 2B).

Figure 2C:
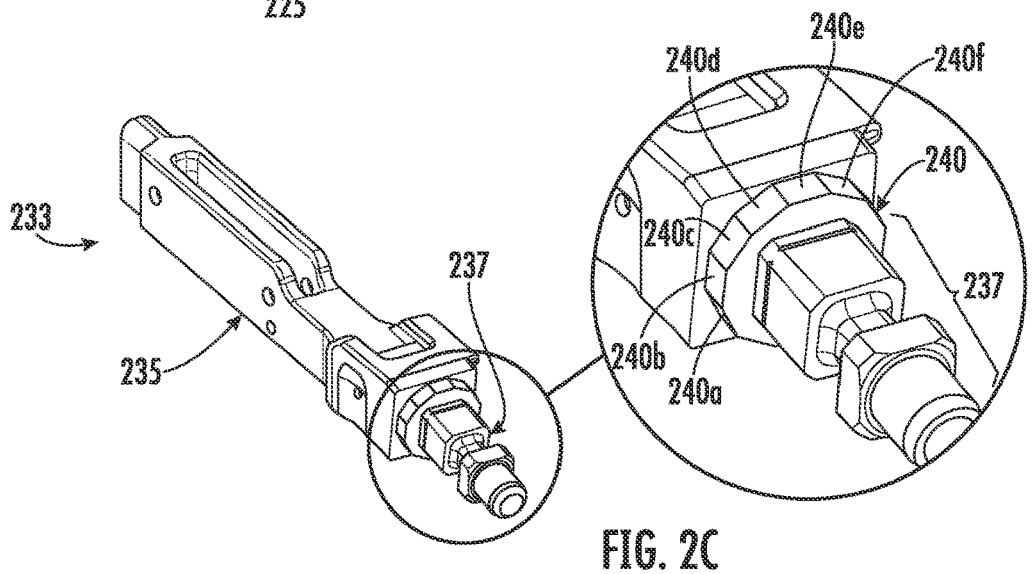
FIG. 2C shows a third adapter for use with the impactor and array of FIG. 1A, including a detail view.

FIG. 2C shows a third adapter 233 for use with the surgical impactor 102 and the array 104 of FIG. 1A. The adapter 233 has a distal portion 235 (e.g., for broaching). The adaptor 233 has a proximal portion 237, which may be retained within a port of the surgical impactor 102 of FIG. 1A in a conventional manner. With reference to the detail view, between the distal portion 235 and the proximal portion 237, a step 240 is provided on the adapter 233. The step 240 may have a non continuous shape, such as a regular polygon with a plurality of facets 240a-f. As can be appreciated, a number of facets in the plurality of facets 240a-f of the step 240 corresponds to a number of offset intervals for the array 104 (e.g., offset relative to a given axis A of the surgical impactor 102, and/or equivalent to potential axes A1-A12 in FIG. 2B). Although not visible, other facets are provided on the step 240 so that the facets are disposed at even intervals around the entire circumference of the step.

In the foregoing embodiments, the above-described arrays are mounted on the above-described adapters. While the array is incapable of moving rotationally (e.g., around the axis defined by the adapter), since the adapter is moving axially (e.g., moving the stroke length of the surgical impactor along the axis defined by the adapter), some movement of the array (e.g., either translationally along the axis defined by the adapter or pivotally (if, for example, a gap develops between the array and the surgical impactor) is possible. Pivotal movement of the array could be addressed by disposing (e.g., interposing) a compressible member between the array and the surgical impactor (e.g., to dampen vibration, as vibration can affect navigational accuracy). In some navigation systems, axial movement of the array may be negligible, e.g., the arrangement may demonstrate a required level of precision (e.g., for determining a position of the array and/or a distal portion of the adapter) regardless.

In some navigation systems, axial movement of the array may be adjusted for (e.g., such as by a control unit or other logic) to achieve a required level of precision (e.g., for determining a position of the array and/or a distal portion of the adapter). For example, the controller may adjust for vibration (the control unit may have an algorithm for averaging measurements because of vibration or may account for stroke length).

The present disclosure further contemplates embodiments where arrays are mounted on surgical impactors. This may be beneficial, for example, if frequent adapter changes are contemplated.

For example, FIG. 3A shows a system 300 comprising a surgical impactor 302 with an array 304. In operation, the surgical impactor 302 may operate substantially as described with respect to FIG. 1A, for example, an adaptor (not depicted) is retained in a port 302a (FIG. 3B) of the surgical impactor 302 to engage the patient (not depicted) in a surgical procedure, such as, for example, a hip or knee arthroplasty. The surgical impactor 302 may be a conventional surgical impactor modified as will be described.

The array 304 is configured to be deployed in a plurality of positions with respect to an axis of the surgical impactor 302, as will be described.

The array 304 comprises a plurality of sockets 306 defined in a frame 308. The sockets 306 are adapted to receive fiducials 309, such as, for example, single-use reflective navigation markers. The fiducials 309 may be used as part of a navigation system, as will be described with respect to FIG. 7, however, in summary, the fiducials enable a position and/or orientation of the array 304 to be determined, which can be extrapolated (e.g., such as by a control unit or other logic) to determine a position and/or orientation of an adapter (not depicted), for example, with reference to a patient. As navigation systems typically operate as optical-based systems (e.g., the fiducials 309 disposed in the sockets 306 are adapted for use with an optical navigation system), maintenance of line of sight between the array 304 and the navigation system is important. For example, during use, the surgical impactor 302 should not be interposed between the array 304 and the navigation system (e.g., to prevent interference with line of sight).

The array 304 also comprises a body 310 which supports the frame 308 and connects the array to the surgical impactor 302 via a collar 311. Referring to FIGS. 3B and 3C, the array 304 may be a two-part system comprising the collar 311 and the body 310 (e.g., integral with the frame 308).

Turning to FIG. 3B, the collar 311 of the array 304 is mounted to the surgical impactor 302 in a manner to prevent rotation of the collar. The collar 311 comprises a sleeve 312 having a plurality of openings 314 defined therein. A ring 316 is disposed adjacent the sleeve 312. The ring 316 does not rotate relative to the sleeve 312 and in practice, the ring and the sleeve may be formed from one piece (e.g., of the collar 311). A plurality of bores 318a-318g are disposed at even intervals around the ring 316. Although not visible, other bores are provided on the ring 316 so that the bores are disposed at even intervals around the entire circumference of the ring.

Turning to FIGS. 3A and 3C, the body 310 of the array 304 has an opening 319 that has a diameter approximately equal to the ring 316 of the collar 311. Although not visible in the figures, a detent protrudes into the opening 319. The body 310 is adapted to be rotatably mountable on the ring 316. When the body 310 is disposed over the ring 316 of the collar 311 (as depicted in FIG. 3A), the detent engages one of the plurality of bores 318a-318g, locking the array 304 in position (e.g., with respect to an axis defined by the surgical impactor 302). In practice, the detent may also keep the opening 319 on the ring 316, although corresponding ridges and grooves are contemplated also, for example, so the body 310 snap fits on the ring.

A detent lock 320 is provided on the body 310 and operably connected to the detent (e.g., to lock the detent into a selected bore of the plurality of bores 318a-318g). In some embodiments, a default position of the detent lock 320 results in the array 304 being locked in place and the detent lock must be depressed to unlock the array from its position (e.g., on the ring 316).

A number of bores of the plurality of bores 318a-318g of the ring 316 corresponds to a number of offset intervals for the array 304 (e.g., three-hundred and sixty degrees divided by the number of bores). By way of a non-limiting example, the array 304 may be offset with respect to an axis of the surgical impactor 302 by intervals of 15 degrees, 22.5 degrees, 30 degrees, 45 degrees, etc., and locked into place at a selected offset. In operation, the array 304 may be unlocked (e.g., using the detent lock 320), and rotated R to a new position corresponding to a new axis with respect to an axis defined by the surgical impactor 302.

Figure 4A:
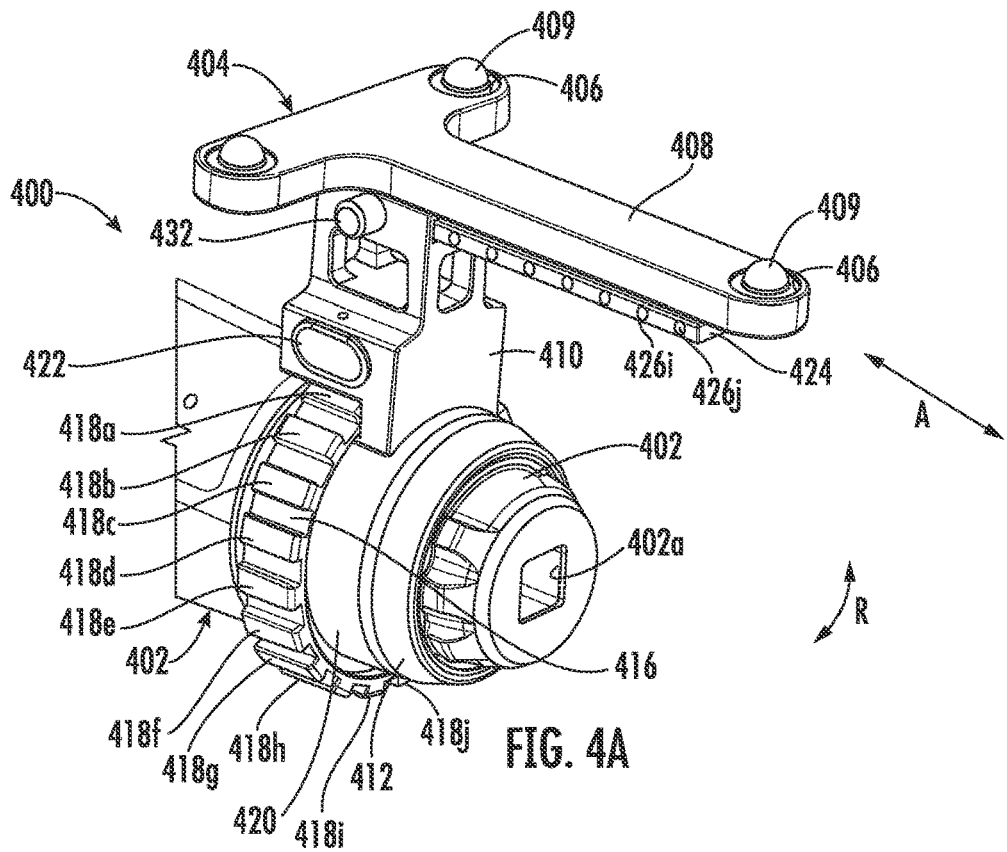
FIG. 4A shows a surgical impactor with yet another embodiment of an associated array that is configured to be deployed in a plurality of positions.
Figure 4B:
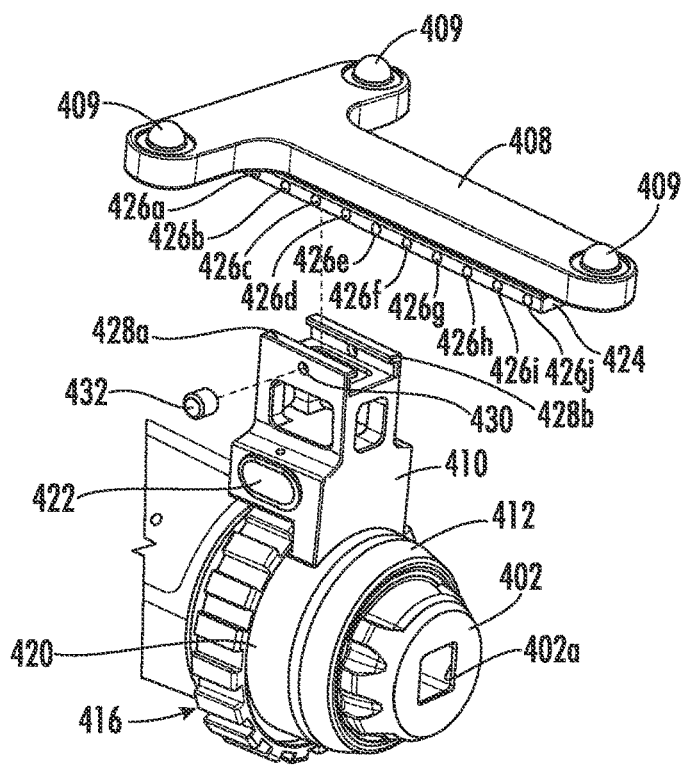
FIG. 4B shows an exploded view of FIG. 4A.

FIGS. 4A and 4B show a surgical impactor 402 with yet another embodiment of an associated array 404 that is configured to be deployed in a plurality of positions along two axes defined by the surgical impactor (e.g., exhibiting a rotational offset R (similar to that described with respect to the foregoing embodiments) and an additional translational offset A).

FIG. 4A shows a system 400 comprising the surgical impactor 402 with the array 404. In operation, the surgical impactor 402 may operate substantially as described with respect to FIG. 1A, for example, an adaptor (not depicted) is retained in a port 402a of the surgical impactor 402 to engage the patient (not depicted) in a surgical procedure, such as, for example, a hip or knee arthroplasty. The surgical impactor 402 may be a conventional surgical impactor modified as described below.

The array 404 is configured to be deployed in a plurality of positions with respect to a first axis and a second axis of the surgical impactor 402, as will be described. The array 404 comprises a plurality of sockets 406 defined in a frame 408. The sockets 406 are adapted to receive fiducials 409, such as, for example, single-use reflective navigation markers. The fiducials 409 may be used as part of a navigation system, as will be described with respect to FIG. 7, however, in summary, the fiducials enable a position and/or orientation of the array 404 to be determined, which can be extrapolated (e.g., such as by a control unit or other logic) to determine a position and/or orientation of an adapter (not depicted), for example, with reference to a patient. As navigation systems typically operate as optical-based systems (e.g., the fiducials 409 disposed in the sockets 406 are adapted for use with an optical navigation system), maintenance of line of sight between the array 404 and the navigation system is important. For example, during use, the surgical impactor 402 should not be interposed between the array 404 and the navigation system (e.g., to prevent interference with line of sight).

The array 404 also comprises a body 410 which supports the frame 408 and connects the array to the surgical impactor 402 via a sleeve 412. The array 404 may be a three-part system comprising the sleeve 412, the body 410, and the frame 408.

The sleeve 412 is mounted to the surgical impactor 402 in a manner to prevent rotation of the sleeve. A ring 416 is disposed adjacent the sleeve 412. The ring 416 does not rotate relative to the sleeve 412 and in practice, the ring and the sleeve may be formed from one piece. A plurality of gear-like protrusions 418a-418j are disposed at even intervals around the ring 416. Although not visible, other protrusions are provided on the ring 416 so that the protrusions are disposed at even intervals around the entire circumference of the ring.

The body 410 of the array 404 has annular portion 420 that has an opening (not visible) with a diameter approximately equal to the sleeve 412. The body 410 is adapted to be rotatably mountable on the sleeve 412. To prevent axial movement (e.g., of the annular portion 420 of the body 410 off the sleeve 412), corresponding ridges and grooves may be disposed on mating surfaces of the annular portion and sleeve, for example, so the body 410 snap fits on the sleeve.

When the body 410 is disposed over the sleeve 412, a stop (not visible in the figures) disposed in the body engages one of the protrusions adjacent to protrusions 418a-418j, locking the array 404 in position (e.g., with respect to a first axis defined by the surgical impactor 402). For example, the stop can be a member adapted to engage between two protrusions (e.g., protrusions adjacent to protrusions 418a-418j) or on either side of a protrusion.

A lock button 422 is provided on the body 410 and operably connected to the stop (e.g., to lock the stop over a selected protrusion adjacent to protrusions 418a-418j or one of the protrusions 418a-418j) In some embodiments, a default position of the lock button 422 results in the array 404 being locked in place and the lock button must be depressed to unlock the array from its position (e.g., with respect to the ring 416).

A number the plurality of protrusions 418a-418j of the ring 416 corresponds to a number of offset intervals for the array 404 (e.g., three-hundred and sixty degrees divided by the number of protrusions or gaps between protrusions). By way of a non-limiting example, the array 404 may be offset with respect to an axis of the surgical impactor 402 by intervals of 15 degrees, 22.5 degrees, 30 degrees, 45 degrees, etc., and locked into place at a selected offset. In operation, the array 404 may be unlocked (e.g., using the lock button 422), and rotated to a new position corresponding to a new axis with respect to a first axis defined by the surgical impactor 402.

The array 404 is also moveable along a second axis defined by the surgical impactor 402. The frame 408 comprises a rail 424 mounted on the opposite side of the frame from the fiducials 409. The rail 424 has a plurality of bores 426a-426j that are disposed at even intervals along the rail.

Turning to FIG. 4B, the body 410 of the array 404 has a pair of clips 428a and 428b for slidingly receiving the rail 424. The pair of clips 428a and 428b cooperate to retain the rail 424 and prevent motion of the rail in any direction other than an axial direction (e.g., with respect to an axis defined by the surgical impactor 402). An opening 430 is disposed below at least one of the clips (and both clips as illustrated), the opening aligning with each of the plurality of bores 426a-426j as the rail 424 moves axially.

A detent lock 432 with a detent (not visible) is provided to protrude through the opening 430 on the body 410 and lock the detent into a selected bore of the plurality of bores 426a-426j. In some embodiments, a default position of the detent lock 432 results in the frame 408 being locked in place and the detent lock must be pulled back to unlock the frame from its position (e.g., with respect to the body 410).

A distance between each of the plurality of bores 426a-426j corresponds to offset intervals (along a second axis defined by the surgical impactor 402) for the frame 408. In operation, the frame 408 may be unlocked (e.g., using the detent lock 432), and the rail 424 slid through the clips 428a and 428b to a new position along a second axis defined by the surgical impactor 402. When the selected position is reached, the detent lock 432 is engaged to lock the detent into a bore of the plurality of bores 426a-426j that is closest to the desired position.

Figure 5A:
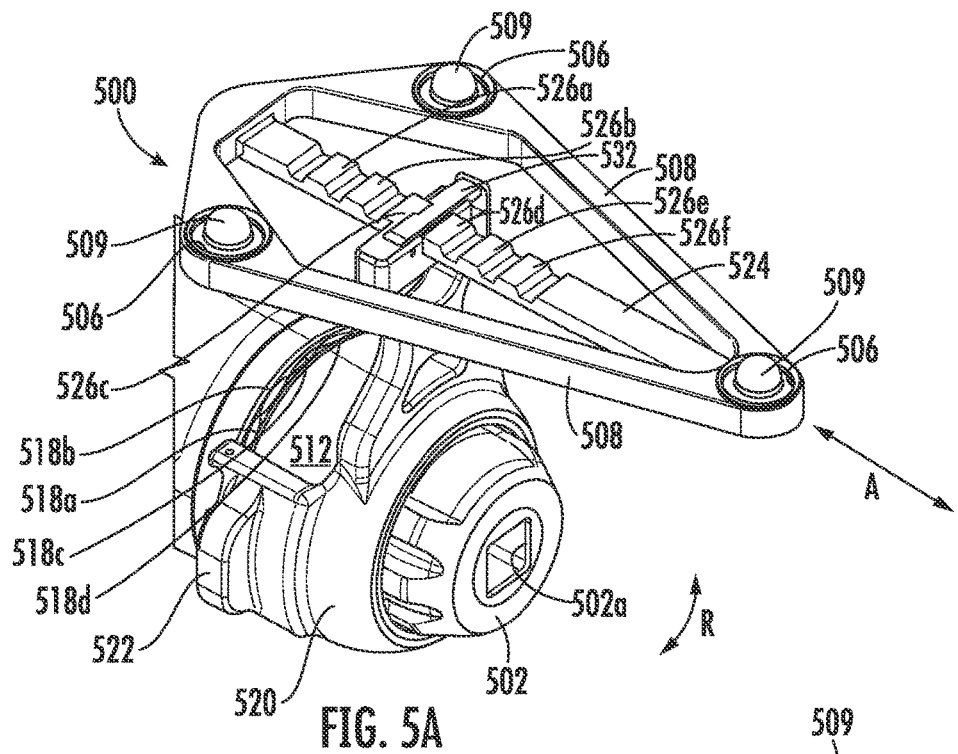
FIG. 5A shows a surgical impactor with yet another embodiment of an associated array that is configured to be deployed in a plurality of positions.
Figure 5B:
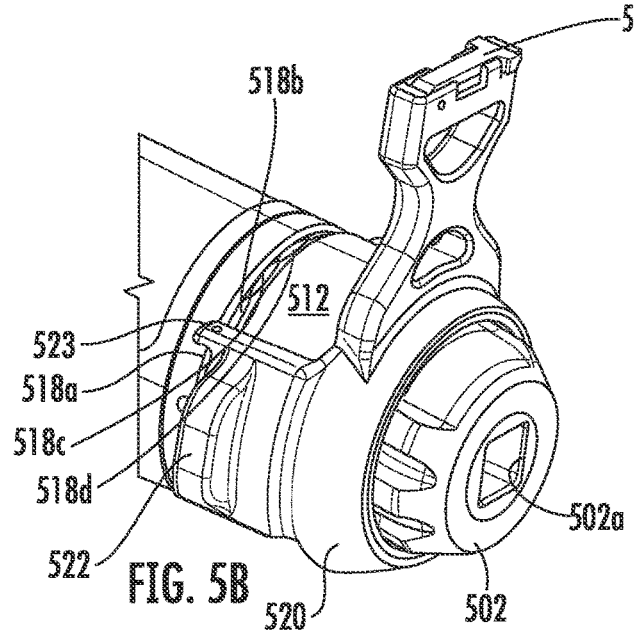
FIG. 5B shows the surgical impactor of FIG. 5A with the array removed.
Figure 5C:
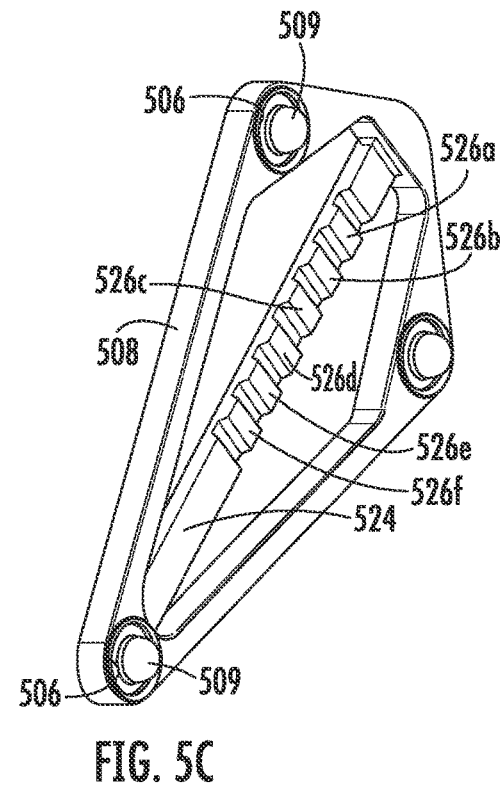
FIG. 5C shows the array of FIG. 5A removed from the surgical impactor.

FIGS. 5A-5C show a surgical impactor 502 with yet another embodiment of an associated array 504 that is configured to be deployed in a plurality of positions along two axes defined by the surgical impactor (e.g., exhibiting a rotational offset R (similar to that described with respect to the foregoing embodiments) and an additional translational offset A). FIG. 5A shows a system 500 comprising the surgical impactor 502 with the array 504. In operation, the surgical impactor 502 may operate substantially as described with respect to FIG. 1A, for example, an adaptor (not depicted) is retained in a port 502a of the surgical impactor 502 to engage the patient (not depicted) in a surgical procedure, such as, for example, a hip or knee arthroplasty. The surgical impactor 502 may be a conventional surgical impactor modified as described below.

The array 504 is configured to be deployed in a plurality of positions with respect to a first axis and a second axis of the surgical impactor 502, as will be described. The array 504 comprises a plurality of sockets 506 defined in a frame 508. The sockets 506 are adapted to receive fiducials 509, such as, for example, single-use reflective navigation markers. The fiducials 509 may be used as part of a navigation system, as will be described with respect to FIG. 7, however, in summary, the fiducials enable a position and/or orientation of the array 504 to be determined, which can be extrapolated (e.g., such as by a control unit or other logic) to determine a position and/or orientation of an adapter (not depicted), for example, with reference to a patient. As navigation systems typically operate as optical-based systems (e.g., the fiducials 509 disposed in the sockets 506 are adapted for use with an optical navigation system), maintenance of line of sight between the array 504 and the navigation system is important. For example, during use, the surgical impactor 502 should not be interposed between the array 504 and the navigation system (e.g., to prevent interference with line of sight).

The array 504 also comprises a body 510 which supports the frame 508 and connects the array to the surgical impactor 502, as will be explained.

Referring to FIGS. 5A and 5B, a sleeve 512 is mounted to the surgical impactor 502 in a manner to prevent rotation of the sleeve. The sleeve 512 has a groove 516 that extends around the circumference of the sleeve. A plurality of facets 518a-d are formed in the bottom of the groove 516. Although not visible, other facets are provided in the groove 516 so that the facets are disposed at even intervals around the entire circumference of the sleeve 512. A number of facets in the groove 516 corresponds to a number of offset intervals for the array, as will be explained.

In some embodiments, the array 504 may be a three-part system comprising the stationary sleeve 512, a rotatable body 510, and an axially moving frame 508.

For example, the body 510 is adapted to be rotatably mountable on the sleeve 512 in offset R. The body 510 may comprise an annular portion 520 for engaging the sleeve 512. The annular portion 520 has an opening (not visible) with a diameter approximately equal to the sleeve 512. A tab 522 extends from the annular portion 520 in the direction of the groove 516. The tab 522 retains a pin 523 which extends from a topmost portion of the tab to a bottommost portion of the tab. The pin 523 engages the groove 516, more specifically, a longitudinal portion of the pin engages a facet (e.g., similar to one of the plurality of facets 518a-d). As can be appreciated, a number of facets in the plurality of facets 518a-d corresponds to a number of offset intervals for the body 510 (e.g., offset relative to a given axis of the surgical impactor 502). Additionally, the pin 523 being retained in the groove 516 prevents axial movement (e.g., of the annular portion 520 of the body 510 off the sleeve 512). Another tab and pin assembly substantially similar to the tab 522 and the pin 523 may be disposed on the other side of the annular portion 520. To rotate the body 510 with respect to the sleeve 512 (and hence the surgical impactor 502), pressure is exerted on the tab 522 to pull the pin 523 away from the facet (e.g., the pin still being retained against a side of the groove 516) and allowing the body to be rotated to a new position (e.g., with respect to a first axis defined by the surgical impactor 502).

A number of the plurality of facets 518a-518d of the sleeve 512 corresponds to a number of offset intervals for the array 504 (e.g., three-hundred and sixty degrees divided by the number of facets). By way of a non-limiting example, the array 504 may be offset with respect to an axis of the surgical impactor 502 by intervals of 15 degrees, 22.5 degrees, 30 degrees, 55 degrees, etc., and locked into place at a selected offset (e.g., via engagement between the pin 523 and the selected facet).

Turning to FIGS. 5A and 5C, the frame 508 of the array 504 is also moveable along a second axis defined by the surgical impactor 502. The frame 508 comprises a rail 524. The body 510 slidingly receives the rail 524. The rail 524 has a plurality of gear-like protrusions 526a-526f that are disposed at even intervals along the rail. A distance between each of the plurality of gear-like protrusions 526a-526f corresponds to offset intervals (along a second axis defined by the surgical impactor 502) for the frame 508.

Turning to FIGS. 5A and 5B, the body 510 has a stop 532 that engages between the protrusions 526c and 526d locking the frame 508 in position. The body 510 and the stop 532 cooperate to retain the rail 524 and prevent motion of the rail (e.g., when secured). In operation, the frame 508 may be unlocked (e.g., using the stop 532), and the rail 524 slid axially to a new position along a second axis A defined by the surgical impactor 502. When the selected position is reached, the stop 532 is engaged to lock between two adjacent protrusions of the plurality of gear-like protrusions 526a-526fj that is closest to the desired position.

Figure 6:
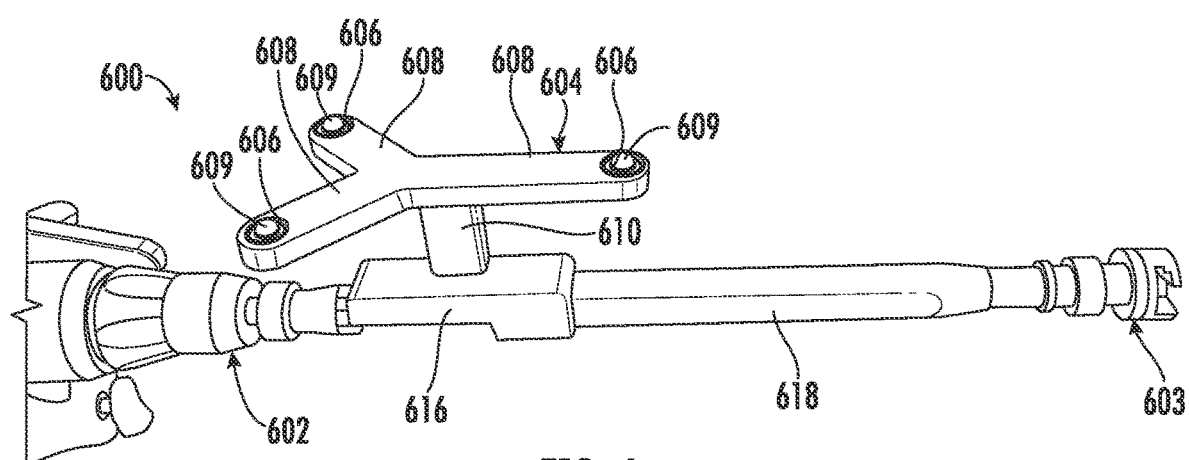
FIG. 6 shows a surgical reamer with an associated array that is configured to be deployed in a plurality of positions.

The above-described embodiments have been described with respect to a surgical impactor, which is a non-rotary tool. FIG. 6 shows a system 600 including a surgical reamer 602 with a rotary cutting tool 603 and an associated array 604 that is configured to be deployed in a plurality of positions along an axis defined between the surgical reamer and the cutting tool. The surgical reamer 602 may be a conventional surgical reamer. The rotary cutting tool 603 may be a conventional cutting tool.

The array 604 is configured to be deployed in a plurality of positions with respect to a first axis of the surgical reamer 602, as will be described. The array 604 comprises a plurality of sockets 606 defined in a frame 608. The sockets 606 are adapted to receive fiducials 609, such as, for example, single-use reflective navigation markers. The fiducials 609 may be used as part of a navigation system, as will be described with respect to FIG. 7, however, in summary, the fiducials enable a position and/or orientation of the array 604 to be determined, which can be extrapolated (e.g., such as by a control unit or other logic) to determine a position and/or orientation of an adapter (not depicted), for example, with reference to a patient. As navigation systems typically operate as optical-based systems (e.g., the fiducials 609 disposed in the sockets 606 are adapted for use with an optical navigation system), maintenance of line of sight between the array 604 and the navigation system is important. For example, during use, the surgical reamer 602 should not be interposed between the array 604 and the navigation system (e.g., to prevent interference with line of sight).

The array 604 also comprises a body 610 which supports the frame 608 and connects the array to the surgical reamer 602, as will be explained. A base 616 is connected to the body 610, and may be slidably disposed on a sheath 618. The base 616 may engage the sheath 618 in a snap-fit, for example, portions of the base (e.g., portions of the base most distal to the frame 608) may deform under force to fit over the sheath and then return to shape to retain the base on the sheath.

The sheath 618 may cover a rotating shaft (not visible) that extends between the surgical reamer 602 and the rotary cutting tool 603 to impart rotational motion to the cutting tool. The sheath 618 may be nonrotatable or may be capable of maintaining a static position despite rotation of the shaft. In some embodiments, the base 616 and the sheath 618 fit tightly together, such that while the base is slidable on the sheath, a predetermined force is required to change the base's axial position on the sheath. In some embodiments, although not visible, the base 616 and the sheath 618 may have cooperating features, such as a stop and associated grooves, to lock the base in position.

The above-described arrays may be part of a computer-assisted surgical system. For example, FIG. 7 shows an overview of a computer-assisted surgical system 700 according to the present disclosure. A surgical robot base 702 supports a robot arm 720. The robot arm 720 includes a plurality of arm segments 704 connected by rotatable or otherwise articulating joints 709. The robot arm 720 can be moved by actuation of the joints, locked in place, etc. Rotation and/or flexion about the joints 709 can allow the robot arm 720 to move in all six degrees of freedom during a procedure. The joints 709 can be configured for incremental changes in each of the six degrees of freedom to ensure precision in operation of a plurality of different end effectors during surgery. The robot arm 720 can actively move about the joints 709 to position arm in a desired position relative to the patient, or the robot arm can be set and locked into a position. For example, the present disclosure is contemplated to include use by surgical robots, by users with some degree of robotic assistance, and without involvement of surgical robots or robotic assistance (e.g., once positioned).

An end effector 708 can be coupled to the robot arm 720. The system 700 can utilize end effectors of various shapes, sizes, and functionalities. Although the end effector 708 is depicted as a surgical impactor (see FIG. 1A et seq.), alternatively, the end effector could be a reamer (FIG. 6). Although not depicted, the end effector 708 can retain a tool (e.g., adapters or cutting tools as described above).

A control unit or controller 712 controls the robot arm 720 and navigational systems. The controller 712 typically includes a power supply, AC/DC converters, motion controllers to power the motors of the actuation units in each joint, fuses, real-time interface circuits, and other components conventionally included in robotic surgical systems. An external device 722 can communicate with the controller 712. The device 722 can be a display, a computing device, remote server, etc., configured to allow a surgeon or other user to input data directly into the controller 712. Such data can include patient information and/or surgical procedure information. The device 722 can display information from the controller, such as alerts. Communication between the device 722 and the controller 712 can be wireless or wired.

The system 700 can utilize an optional navigation array 706 mounted on the robot arm 720 to determine a position of the end effector 708. The structure and operation of the navigation array 706 can vary depending on the type of navigation system used. In some embodiments, the navigation array 706 can include one or more sphere-shaped or other fiducials for use with an optical navigation system, for example, a robotic navigation system. The navigation system can facilitate registering and tracking of the position and/or orientation of the navigation array 706 and, by extension, the end effector 708 and its relative distance to other objects in the operating room, e.g., a patient, a surgeon, etc.

The end effector 708 has a navigation array 707 (such as the above-described array 104, the array 304, the array 404, the array 504, and/or the array 604) that can be directly attached to the end effector. The navigation system can facilitate registering and tracking of the position and/or orientation of the navigation array 707. Advantageously, the array 707 can be re-positioned with respect to at least one axis of the end effector 708. The re-positioning may be achieved without removing the end effector 708 from the robot arm 720. It is understood that in some embodiments (in particular such as the array 104), the array may be vibrating from the impactor, however, the controller may adjust for vibration (the controller may have an algorithm for averaging measurements because of vibration or may account for stroke length).

Fiducials of the array 707 can be arranged in predetermined positions and orientations with respect to one another. The fiducials can be aligned to lie in planes of known orientation (e.g., perpendicular planes, etc.) to enable setting of a Cartesian reference frame. The fiducials can be positioned within a field of view of a navigation system and can be identified in images captured by the navigation system. Exemplary fiducials include infrared reflectors, light emitting diodes (LEDs), spherical reflective markers, blinking LEDs, augmented reality markers, and so forth. The navigation arrays can be or can include an inertial measurement unit (IMU), an accelerometer, a gyroscope, a magnetometer, other sensors, or combinations thereof. The sensors can transmit position and/or orientation information to a navigation system, e.g., to a processing unit of the navigation system, which can, for example be the controller 712.

The system 700 can also comprise a tracking unit 714, such that the relative pose or three-dimensional position and orientation of the navigation array 706 (and/or other navigation arrays) can be tracked in real time and shared to the controller 712 for planning or control. The tracking unit 714 can measure the relative motions between any and all components coupled to navigation arrays in a known manner. Tracking can be performed in a number of manners, e.g., using stereoscopic optical detectors 716, ultrasonic detectors, sensors configured to receive position information from inertial measurement units, etc. Tracking in real time can, in some embodiments, mean high frequencies greater than twenty Hertz, in some embodiments in the range of one hundred to five hundred Hertz, with low latency, in some embodiments less than five milliseconds. Regardless of how it is gathered, position and orientation data can be transferred between components (e.g., to the controller 712) via any suitable connection, e.g., with wires or wirelessly using a low latency transfer protocol. The real-time controller 712 can carry out real-time control algorithms at a reasonably high frequency with low additional latency to coordinate movement of the system 700. The tracking unit can also include cameras, or use the stereoscopic optical detectors 716, to detect, for example, a shape and/or a dimension of the end effector 708.

Examples of the above-described embodiments can include the following.

In a first example, a navigational array for attaching to a surgical tool, comprises a frame comprising fiducials for detection by an optical navigation system, and a body having a first end for supporting the frame and a second end defining an opening, wherein the opening is aligned with a first axis of the surgical tool, wherein the opening engages a stationary surface adjacent to the surgical tool, and wherein the opening engages features disposed at predetermined even intervals on the stationary surface adapted to allow repositioning of the array from a first position to a second position, wherein the second position is at least one of a rotational offset or an axial offset from the first position. In some examples, the stationary surface is a step disposed on an adapter inserted into the surgical tool. In some examples, the step is a regular polygon-shaped step (e.g., octagon-shaped step, dodecagon-shaped step, etc.) and the opening has a cooperating shape. In some examples, the stationary surface is a sheath covering a rotatable shaft inserted into the surgical tool.

In a second example, a navigational array for attaching to a surgical tool, comprises a frame comprising fiducials for detection by an optical navigation system, a body having a first end for supporting the frame and a second end defining an opening, and a non-rotatable symmetrical sleeve disposed on the surgical tool, wherein the opening and sleeve are aligned with a first axis of the surgical tool, and wherein the opening engages features disposed at predetermined even intervals on the sleeve adapted to allow repositioning of the array from a first position to a second position, wherein the second position is a rotational offset from the first position. In some examples, the sleeve defines a plurality of bores around a circumference of the sleeve. In some examples, the opening retains a detent for engaging a bore of the plurality of bores. In some examples, the body further comprises a button to disengage the detent, thereby allowing rotation of the body around the sleeve. In some examples, the sleeve defines a plurality of protrusions around a circumference of the sleeve. In some examples, the opening retains a stop for engaging a space between two protrusions of the plurality of protrusions. In some examples, the body further comprises a button to disengage the stop, thereby allowing rotation of the body around the sleeve. In some examples, the sleeve defines a plurality of facets around a circumference of the sleeve. In some examples, the opening retains a stop for engaging a space between two protrusions of the plurality of protrusions. In some examples, the body further comprises a button to disengage the stop, thereby allowing rotation of the body around the sleeve. In some examples, the frame and the body are fixed in position with respect to each other.

In a third example, a navigational array for attaching to a surgical tool, comprises a frame comprising fiducials for detection by an optical navigation system, a body having a first end for supporting the frame, wherein the frame is adapted to move with respect to the body along a first axis of the surgical tool, and a second end defining an opening, and a non-rotatable symmetrical sleeve disposed on the surgical tool, wherein the opening and sleeve are aligned with the first axis of the surgical tool, and wherein the opening engages features disposed at predetermined even intervals on the sleeve adapted to allow repositioning of the array from a first position to a second position, wherein the second position is a rotational offset from the first position. In some examples, the frame further comprises a rail slidingly disposed on the body. In some examples, the rail defines a plurality of bores, and wherein the body retains a detent for engaging a bore of the plurality of bores. In some examples, the rail defines a plurality of protrusions, and wherein the body retains a stop for engaging a space between two protrusions of the plurality of protrusions.

In a fourth example, a surgical system comprises a navigational array for attaching to a surgical tool, comprises a frame comprising fiducials for detection by an optical navigation system, and a body having a first end for supporting the frame and a second end defining an opening, wherein the opening is aligned with a first axis of the surgical tool, wherein the opening engages a stationary surface adjacent to the surgical tool, and wherein the opening engages features disposed at predetermined even intervals on the stationary surface adapted to allow repositioning of the array from a first position to a second position, wherein the second position is at least one of a rotational offset or an axial offset from the first position, an optical navigation system, and a controller adapted to use the navigation system to track of the position and/or orientation of the array.

The invention claimed is:

1. A navigational array for attaching to a surgical tool, comprising:
   a frame comprising fiducials for detection by an optical navigation system; and
   a body having a first end for supporting the frame and a second end defining an opening,
   wherein the opening is aligned with a first axis of the surgical tool,
   wherein the opening engages a stationary surface adjacent to the surgical tool, and
   wherein the opening engages features disposed at predetermined even intervals on the stationary surface adapted to allow repositioning of the array from a first position to a second position, wherein the second position is at least one of a rotational offset or an axial offset from the first position.

2. The navigational array of claim 1, wherein the stationary surface is a sheath covering a rotatable shaft inserted into the surgical tool.

3. The navigational array of claim 1, wherein the stationary surface is a step disposed on an adapter inserted into the surgical tool.

4. The navigational array of claim 3, wherein the step is a regular polygon-shaped step and the opening has a cooperating shape.

5. A surgical system comprising:
   the array of claim 1;
   an optical navigation system; and
   a controller adapted to use the navigation system to track of the position and/or orientation of the array.

6. A navigational array for attaching to a surgical tool, comprising:
   a frame comprising fiducials for detection by an optical navigation system;
   a body having a first end for supporting the frame and a second end defining an opening; and
   a non-rotatable symmetrical sleeve disposed on the surgical tool,
   wherein the opening and sleeve are aligned with a first axis of the surgical tool, and
   wherein the opening engages features disposed at predetermined even intervals on the sleeve adapted to allow repositioning of the array from a first position to a second position, wherein the second position is a rotational offset from the first position.

7. The navigational array of claim 6, wherein the frame and the body are fixed in position with respect to each other.

8. The navigational array of claim 6, wherein the sleeve defines a plurality of bores around a circumference of the sleeve.

9. The navigational array of claim 8, wherein the opening retains a detent for engaging a bore of the plurality of bores.

10. The navigational array of claim 9, wherein the body further comprises a button to disengage the detent, thereby allowing rotation of the body around the sleeve.

11. The navigational array of claim 6, wherein the sleeve defines a plurality of protrusions around a circumference of the sleeve.

12. The navigational array of claim 11, wherein the opening retains a stop for engaging a space between two protrusions of the plurality of protrusions.

13. The navigational array of claim 12, wherein the body further comprises a button to disengage the stop, thereby allowing rotation of the body around the sleeve.

14. The navigational array of claim 6, wherein the sleeve defines a plurality of facets around a circumference of the sleeve.

15. The navigational array of claim 14, wherein the opening retains a stop for engaging a space between two protrusions of the plurality of protrusions.

16. The navigational array of claim 15, wherein the body further comprises a button to disengage the stop, thereby allowing rotation of the body around the sleeve.

17. A navigational array for attaching to a surgical tool, comprising:
   a frame comprising fiducials for detection by an optical navigation system;
   a body having a first end for supporting the frame, wherein the frame is adapted to move with respect to the body along a first axis of the surgical tool, and a second end defining an opening; and
   a non-rotatable symmetrical sleeve disposed on the surgical tool,
   wherein the opening and sleeve are aligned with the first axis of the surgical tool, and
   wherein the opening engages features disposed at predetermined even intervals on the sleeve adapted to allow repositioning of the array from a first position to a second position, wherein the second position is a rotational offset from the first position.

18. The navigational array of claim 17, wherein the frame further comprises a rail slidingly disposed on the body.

19. The navigational array of claim 18, wherein the rail defines a plurality of bores, and wherein the body retains a detent for engaging a bore of the plurality of bores.

20. The navigational array of claim 18, wherein the rail defines a plurality of protrusions, and wherein the body retains a stop for engaging a space between two protrusions of the plurality of protrusions.

* * * * *